US010556734B2

(12) United States Patent
Steins (10) Patent No.: US 10,556,734 B2
(45) Date of Patent: Feb. 11, 2020

(54) ULTRASOUND TRANSMISSION GEL PACKET HAVING INTERNAL HEAT SOURCE AND METHOD OF USE

(71) Applicant: Robert Steins, Seattle, WA (US)

(72) Inventor: Robert Steins, Seattle, WA (US)

(*) Notice: Subject to any disclaimer, the term of this patent is extended or adjusted under 35 U.S.C. 154(b) by 154 days.

(21) Appl. No.: 15/638,199

(22) Filed: Jun. 29, 2017

(65) Prior Publication Data

US 2018/0002096 A1 Jan. 4, 2018

Related U.S. Application Data

(60) Provisional application No. 62/356,411, filed on Jun. 29, 2016.

(51) Int. Cl.
*A61B 8/00* (2006.01)
*B65D 81/18* (2006.01)
*A61M 35/00* (2006.01)
*B65D 75/38* (2006.01)
*B65D 81/32* (2006.01)

(52) U.S. Cl.
CPC ............ *B65D 81/18* (2013.01); *A61B 8/4272* (2013.01); *A61M 35/00* (2013.01); *B65D 75/38* (2013.01); *B65D 81/3266* (2013.01); *A61M 2205/0288* (2013.01); *A61M 2205/0294* (2013.01); *A61M 2205/364* (2013.01); *A61M 2205/3673* (2013.01); *A61M 2205/3686* (2013.01); *A61M 2205/3693* (2013.01)

(58) Field of Classification Search
CPC .............. A61K 49/226; C12N 15/1006; A61B 8/4281; A61B 8/4272; A61M 2205/364; A61M 2205/3673; A61M 2205/3693; A61M 35/00; B65D 75/38; B65D 81/18; B65D 81/3266
USPC .................................................. 126/263.02
See application file for complete search history.

(56) References Cited

U.S. PATENT DOCUMENTS 5,366,491 A * 11/1994 Ingram ..................... A61F 7/02
126/204
2016/0192901 A1* 7/2016 O'Boyle, Jr. ........ A61B 8/4281
600/437

* cited by examiner

*Primary Examiner* — Avinash A Savani
(74) *Attorney, Agent, or Firm* — Steins & Associates, P.C.

(57) ABSTRACT

An Ultrasound Transmission Gel Packet Having Internal Heat Source and Method of Use. The gel packet is sized for a single use, rather than for multiple applications. The gel packets are not pre-heated, but rather are quickly heatable on demand. The gel packets may incorporate a variety of optional internal heating methods, including chemical activation, mechanical agitation and electrical activation, among others. The gel packets are sealed and therefore have extended shelf lives, and further are disposable after use.

20 Claims, 5 Drawing Sheets

ULTRASOUND TRANSMISSION GEL PACKET HAVING INTERNAL HEAT SOURCE AND METHOD OF USE

This application is filed within one year of, and claims priority to Provisional Application Ser. No. 62/356,411, filed Jun. 29, 2016.

BACKGROUND OF THE INVENTION

1. Field of the Invention

This invention relates generally to medical devices and procedures and, more specifically, to an Ultrasound Transmission Gel Packet Having Internal Heat Source and Method of Use.

2. Description of Related Art

Figures 1, 2:
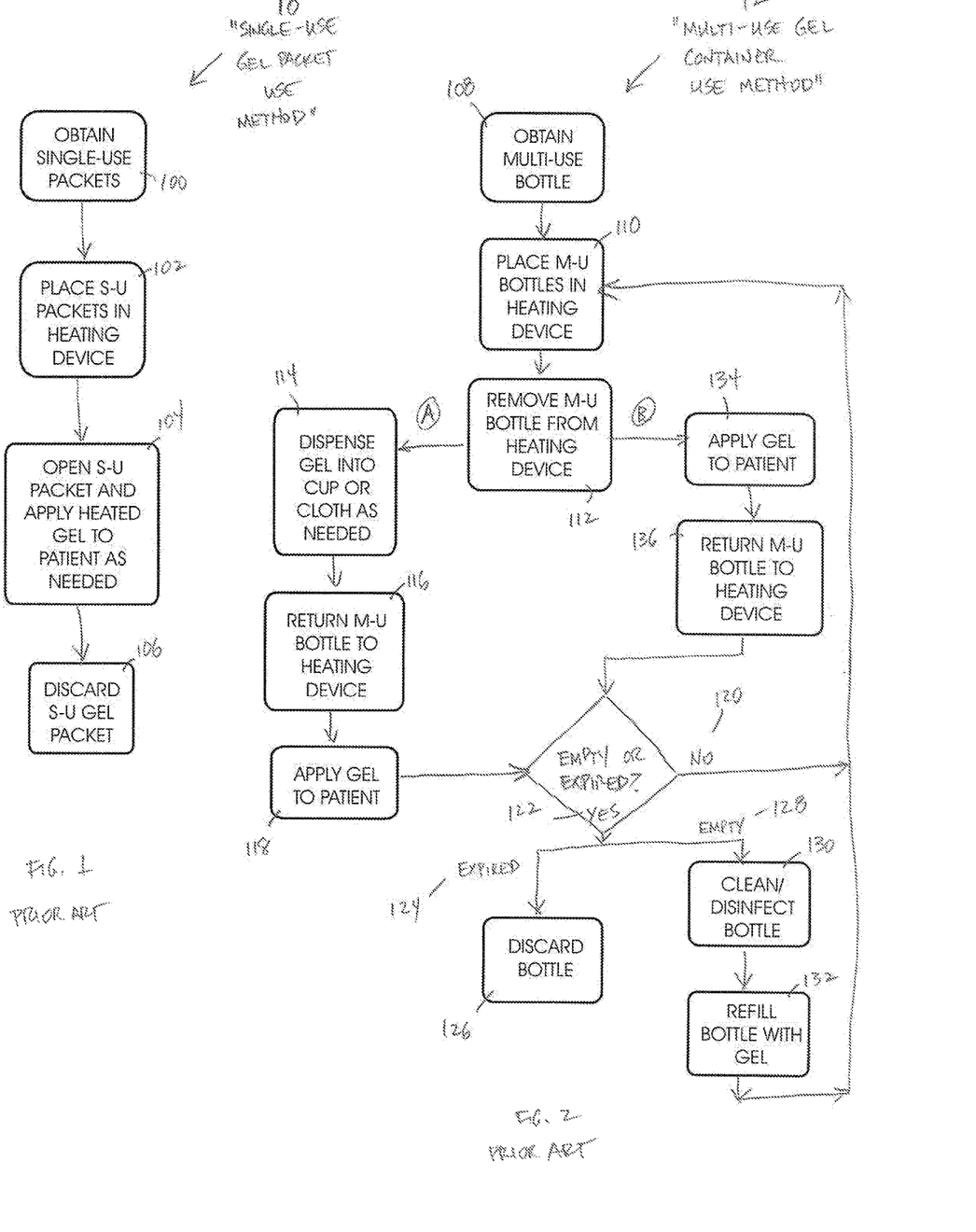
FIG. 1 is a flowchart depicting the conventional single-use gel packet use method.
FIG. 2 is a flowchart depicting the conventional multi-use gel packet use method.

The use of ultrasound technology for the purpose of diagnostic imaging is performed in virtually every hospital and most urgent care facilities in the world. Furthermore, ultrasound scanning is conducted in most of the treatment areas within each health care facility. Because sound does not travel well in air, physicians and technologists performing an ultrasound examination routinely apply a conductive gel to the subject area prior to placing the ultrasound probe against the patient's body. For comfort and other safety reasons (e.g. thermal stress to neonatal infants[1]), it is a common practice for health care facilities to pre-warm the conductive gel prior to patient application. FIGS. 1 and 2 provide the background of how the gel is heated.

[1] "Procedural Hazards of Neonatal Ultrasonography" *J Clin Ultrasound.* 1986 June; 14 (5):361-6.

Single-use gel packages are often used for dispensing ultrasound gel. FIG. 1 is a flowchart depicting the conventional single-use gel packet use method 10. Once obtained 100, the single-use gel packets are typically placed into a dedicated gel-pak warmer 102. When gel is needed in order to perform an ultrasound scan on a patient, the heated gel packet is retrieved from the warmer, opened, and the heated gel is applied to the patient 104. The expended gel packet is then discarded 106.

In some facilities or environments, multi-use dispensers (e.g. bottles or other containers) of ultrasound gel are employed. FIG. 2 is a flowchart depicting the conventional multi-use gel container use method 12. The multi-use container is obtained 108 and placed into the warming device 110, where it/they reside until gel is needed. When desired, the bottle is removed from the heating device 112, and the heated gel is either applied directly to the patient 134(and then the bottle returned 136), or first into a cup or cloth 114, and then to the patient 118 (usually after returning the bottle to the heating device 116). This process is repeated until the bottle/container is empty or expired 122. Expired bottles 124 are discarded 126. Empty bottles 128 are cleaned and/or disinfected 130, refilled 132, and returned to service.

The problem with these conventional use methods is the prevention of gel contamination. Both methods include a shared or community heating device, typically a water bath or oven, which are known breeding grounds for pathogens. This can easily result in patients contracting a nosocomial infection.[2] While a number of procedures have been developed to curtail this risk, gel bottle warmers continue to be a significant source of nosocomial infection.

[2] See Appendix I

What is needed is a more sanitary heated gel package and method of use.

SUMMARY OF THE INVENTION

In light of the aforementioned problems associated with the prior devices and methods, it is an object of the present invention to provide an Ultrasound Transmission Gel Packet Having Internal Heat Source and Method of Use. The gel packet should be sized for a single use, rather than for multiple applications. The gel packets ideally should not be pre-heated, but rather should be quickly heatable on demand. The gel packets should incorporate a variety of optional internal heating methods, including chemical activation, mechanical agitation and electrical activation, among others. The gel packets should be sealed and therefore have extended shelf lives, and further should be disposed of after use.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings, of which:

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an Ultrasound Transmission Gel Packet Having Internal Heat Source and Method of Use.

Figure 3:
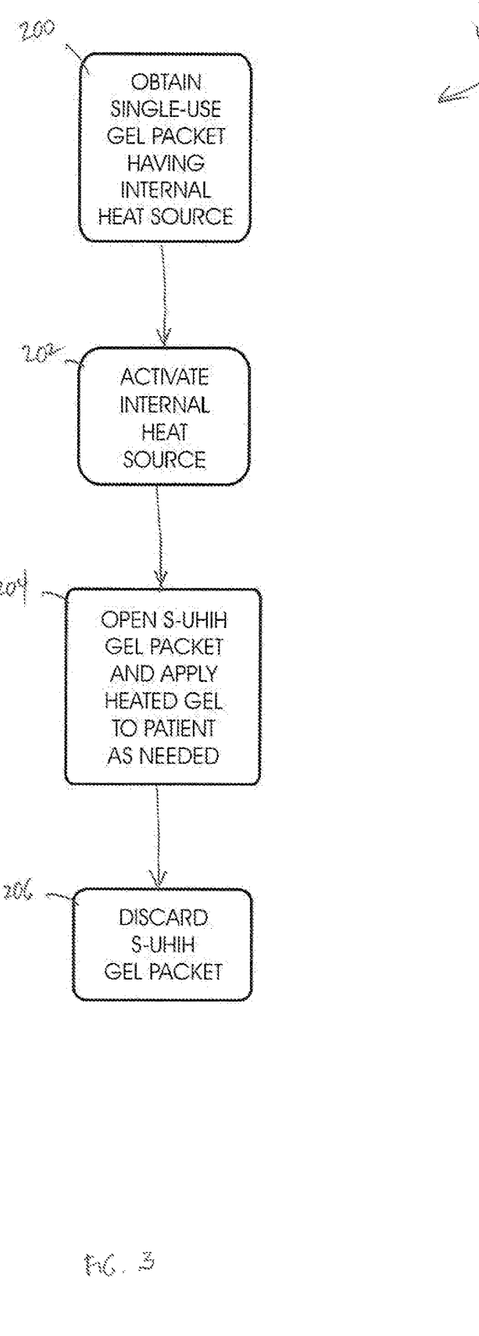
FIG. 3 is a flowchart depicting a preferred method of use of the single-use individually-heatable gel packets.

The present invention can best be understood by initial consideration of FIG. 3.[3] FIG. 3 is a flowchart depicting a preferred method of use of the single-use individually-heatable gel packets 14. As discussed previously, the purpose of the instant method and device is to reduce the level of risk of nosocomial infection created by the process steps and the components involved in the heating of ultrasound gel.

[3] As used throughout this disclosure, element numbers enclosed in square brackets [ ] indicates that the referenced element is not shown in the instant drawing figure, but rather is displayed elsewhere in another drawing figure.

The initial step in this new process involves obtaining a single-use gel packet that has an internal heat source 200. The design specifics of the individually, internally-heated gel packet will be discussed below in connection with other drawing figures, however, it is sufficient to understand that there is no oven or other water bath involved in the packet-heating process. Each packet is individually heated on an as needed basis in order to minimize the growth and transfer of contaminating microorganisms, as has been shown to be a problem with the prior methods and devices. Consequently, the packages can remain in a hygienic environment until they are removed from the storage container for use.

Figure 4:
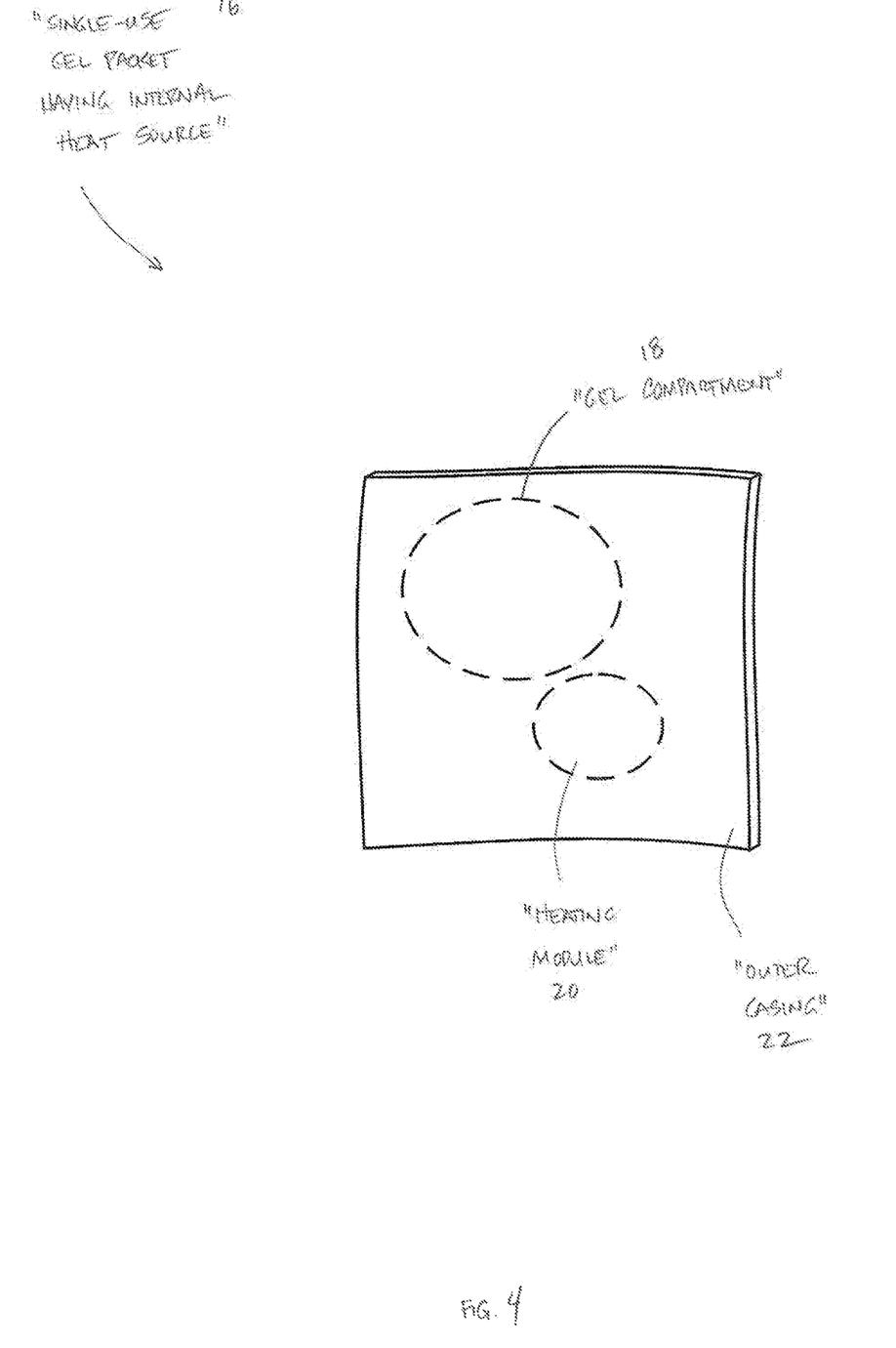
FIG. 4 is a functional perspective view of a single-use gel packet having an internal heat source.

The user first obtains a single gel packet of the type described herein below 200. The internal heat source is then activated within the gel packet 202. Next, the operator (typically a sonographer or sonologist) opens the gel packet, dispenses the heated gel and applies it to the patient in the area to be scanned 204. Finally, the operator discards the empty gel package 206. The steps 200-206 are repeated for each dispensing of heated gel. It should also be noted that if the operator deems that heated gel is not desirable, he or she simply opens the packet and applies the gel without first heating the gel. This additional benefit means that the operator only requires a single source of gel packets, rather than being required to maintain separate inventories of heated and unheated gel packages. FIG. 4 introduces the gel packets used in this process 14.

FIG. 4 is a functional perspective view of a single-use gel packet having an internal heat source 16. The packet 16 is preferably has an outer casing 22 made from sterile, disposable materials. Within the casing, there is a gel compartment 18 and a heating module 20. As discussed below, the heating module 20 may actually be incorporated into the outer casing 22, such as to form the gel compartment 18, in certain versions.

Figure 5:
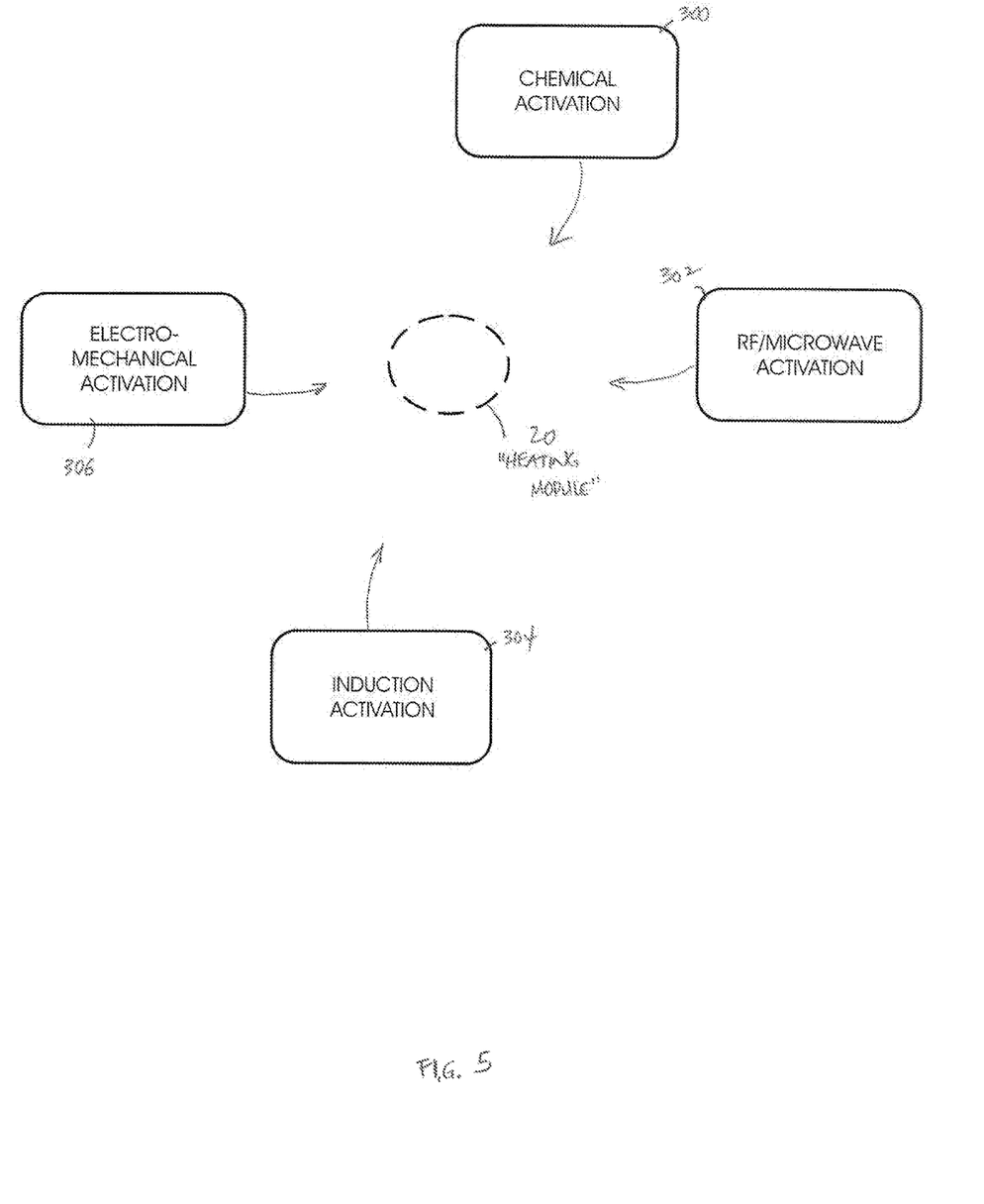
FIG. 5 is a diagram showing optional heating options for the internal heat source of the gel packet of the present invention.

FIG. 5 is a diagram showing optional heating options for the internal heat source of the gel packet of the present invention. One preferred version of the heating module 20 is by chemical activation—that is to say that the gel in the compartment [18] would generally be mixed with a second chemical component (in a second gel compartment [18]). When mixed, the two components would generate a desirable amount of heat as a result of the exothermic reaction. This version is more fully described below in connection with FIG. 6.

The heating module 20 could also comprise electrical induction activation 304. This version may have coiled electrical filaments embedded within the casing [22] and/or gel compartment [18], or even as a series of filaments actually protruding into the gel compartment [18] itself. The heating mechanism could be via induction. If a gel package having such a heating module 304 is placed into a magnetic field, the field will cause current to flow through the electrical filaments. The filaments and package will be designed so that they will begin to heat up as current is generated, thereby heating the gel in the compartment [18] to the desired temperature. The magnetic field generator could be operated automatically to turn its magnetic field on when a new packet is placed in a predetermined location, and then turn off automatically either after a preset time is reached, or after a preset temperature is reached.

In another version, the heating module 20 could heat through electro-mechanical means 306. In this embodiment, a piezoelectric device would be embedded within the casing [22] or would protrude into the gel compartment [18] itself. When connected to an electrical energy source, the piezoelectric device converts electrical energy into mechanical vibration, thereby generating heat in the gel.[4,5] The energy source could be operated automatically to activate the piezoelectric element or elements when the packet is placed in a predetermined location, and then turn off automatically either after a preset time is reached, or after a preset temperature is reached.

[4] Eduardo Moros, ed., *Physics of thermal therapy: fundamentals and clinical applications*, Imaging in medical diagnosis and therapy (Boca Raton, Fla.: CRC/Taylor & Francis, 2013), 81-82.

[5] Visvanathan, Karthik, and Yogesh B. Gianchandani "Microheaters based on ultrasonic actuation of piezoceramic elements." *Journal of Micromechanics and Microengineering* 21.8 (2011): 085030.

Finally, the heating module 20 may generate heat via RF or microwave activation. In this version, the gel package would be placed within an RF or microwave-generating device. The casing [22] would need to be made from material that is compatible with RF or microwave energy generation. Furthermore, there would need to be safety features, such as overtemp protection and/or room for expansion of the gel as it heats within the compartment [18] in order to prevent the inadvertent explosion of a gel package during the heating process.

Figure 6:
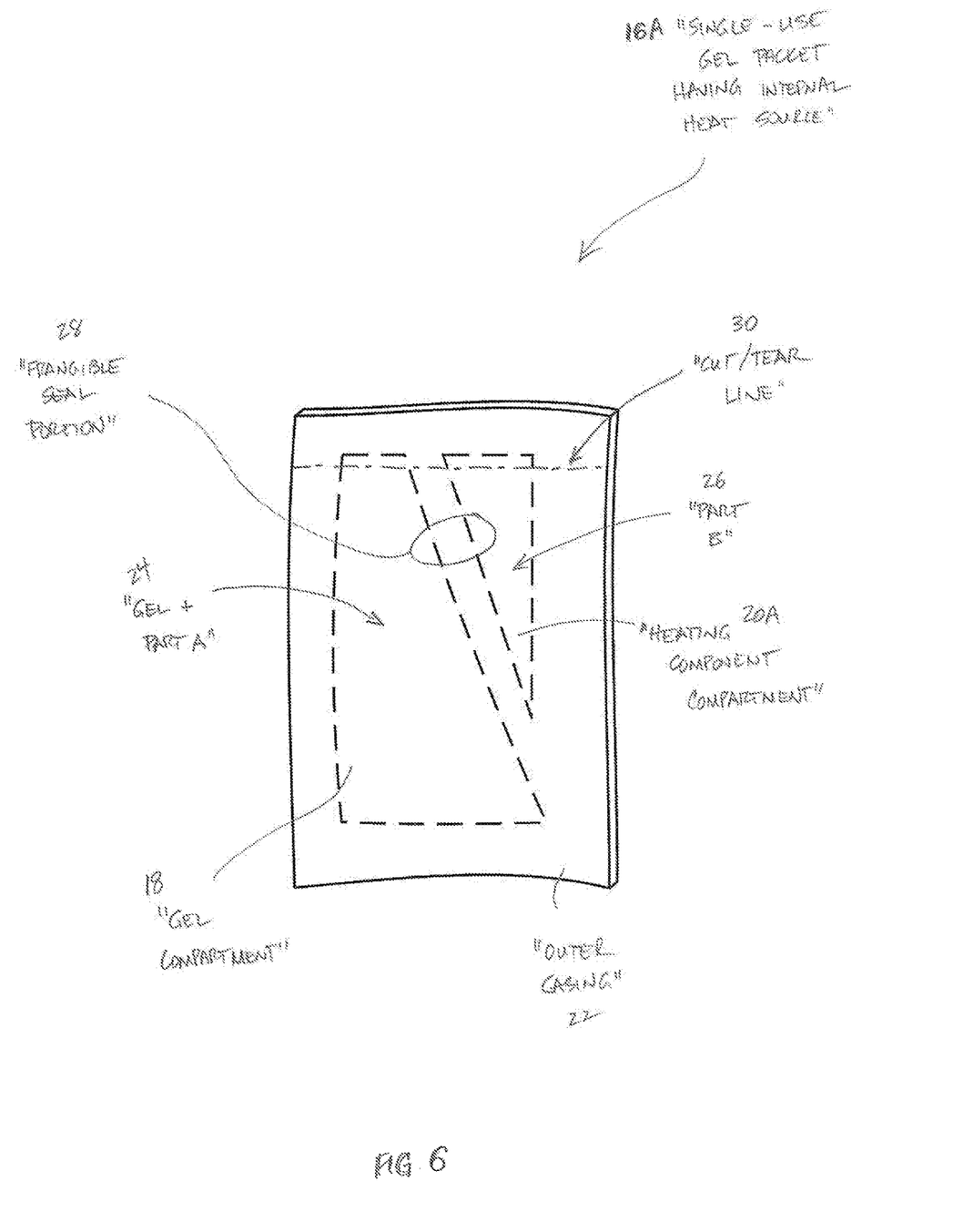
FIG. 6 is a perspective view of a preferred embodiment of a chemically-activated version of the gel packet of FIG. 4.

If we now turn to FIG. 6, we can more closely examine the features of the chemically activated heating module version 300. FIG. 6 is a perspective view of a preferred embodiment of a chemically activated version 16A of the gel packet of FIG. 4. T The outer casing 22 will house a two-part gel compartment 18. As discussed previously, there will be a gel compartment 18 and a heating component compartment 20A. Part A of the gel 24 will be in the gel compartment 18. Part B of the gel 26 will be contained within the heating component compartment 20A. The two compartments 18, 20A will be separated by a separation portion 29 of the outer casing 22.

In its preferred form, the packet 18A will have a frangible seal portion 28 that makes up at least a part of the separation portion 29. This frangible seal portion 28 is designed so that the operator can cause a port to be created between the gel compartment 18 and heating component compartment 20A without breaking open the outer casing 22. Once the port between the two compartments 18, 20A is created (e.g. by some sort of hand manipulation of the package 18A by the operator), the two parts of the gel 24, 26 will come into contact with one another so that they will mix. The parts 24, 26 are designed to generate heat when they mix with each other.

There are several possible chemical compositions for warming gel. One possible composition utilizes an acid-base neutralization reaction. These reactions are typically highly exothermic when between a weak acid and strong base, or between a strong acid and weak base. Depending on the specific acids and bases used, the composition could be engineered to leave a neutral pH reaction-this ideally would stay in solution and be non-toxic (e.g. the resulting products of the reaction would be saltwater). This would require a gel, an acidic solution, and a basic solution to be stored in separate compartments prior to activation (each compartment would be separated from the others by inter-compartmental seals/walls). To activate heat generation, the seal between the acid and base would be broken, allowing the neutralization reaction to take place, producing a salt solution hotter than 40° C., which would then be mixed with a very thick gel by breaking a second frangible seal in the package containing the gel.

Another possible form of heating the gel utilizes an exothermic reaction via introduction of catalyst(s) whereby heat is produced through polymerizations. In a preferred form, the dissolution of an anhydrous salt into the gel is an effective method of warming. The two salts that have the highest enthalpy of solution are calcium chloride and magnesium chloride. On the assumption that the mass of the gel is 30 g and that it's heat capacity is 4.18 J/(K·g), the required enthalpy to heat the gel from 21° C. to 40° C. is calculated using Equation 1 below:

$$\Delta H = c_p \cdot m \cdot \Delta T = 4.18 \frac{J}{K \cdot g} \cdot 30 \text{ g} \cdot 19 \text{ K} = 2383 \text{ J}$$

Based upon the standard enthalpies of formation, the standard enthalpies of the solution for anhydrous calcium chloride and anhydrous magnesium chloride are −82.0 kJ/mol and −155.0 kJ/mol, respectively. Thus, using the molar masses of the two salts, the amount of salt needed to achieve a 19° C. temperature increase is 3.23 g of calcium chloride or 1.46 g of magnesium chloride. The difference in masses between salt types shows that the use of magnesium chloride would decrease the mass of salts required and, as discussed below, would likely decrease both the activation time and the introduction of air into the gel. The theoretical numbers for each salt are detailed in Table I below.

TABLE I

Theoretical Salt Requirements

| Compound | Standard enthalpy of solution (kJ/mol) | Molar Mass (g) | Required Mass (g) |
|---|---|---|---|
| Calcium Chloride (anhydrous) | −82.0 | 111.0 | 3.23 |
| Magnesium Chloride (anhydrous) | −155.0 | 95.2 | 1.46 |

Several additional viable formulations have been developed, with all containing similar ingredients. All of the formulations contain a cellulosic thickener, glycerin, deionized water, sodium benzoate, and an anhydrous salt. Two different thickeners were used including Natrosol 250 HHR (a hydroxyethylcellulose), and KELTROL CG-T (a xanthan gum). Both of the thickeners are used in a wide range of products, and are very pH stable. Because these thickener products are nonionic, their combination with salts will not affect their ability to thicken into a gel. Glycerin, which acts as a stabilizer and emulsifier, is also a common additive in many cosmetic formulations. It aids in keeping the hydroxyethylcellulose or xanthan gum stable in the gel. Sodium benzoate, which is a common preservative and is compatible with both Natrosol 250 HHR and xanthan gum.

Continuing with preferred form options, a two-part system for heating of clear gel by the addition of an anhydrous salt is described. This is a two-part formulation which consists of a base gel, which, when mixed with an anhydrous salt, heats up to about 40° C. (depending on ambient storage temperature). After activation, these gel formulations have viscosities at 37° C. that are similar to current products on the market, such as Aquasonic 100, Aquasonic Clear, and Clear Image Singles, which all range from 35000-41000 cP. Two variations of this formulation were prepared and tested. The first was a two-part formulation which consisted of a gel made with hydroxyethylcellulose (HEC, Natrosol 250 HHR), glycerin, and sodium benzoate. Hydroxyethylcellulose is a cellulosic thickener used in a wide range of industries and used in levels ranging from 0.1-3.0%. It is stable in the pH range of 2-12, and its ability to thicken into a gel is nonionic, therefore salts do not affect its viscosity. Glycerin is a common additive to many cosmetic formulations as a stabilizer and emulsifier that stabilizes the hydroxyethylcellulose within the gel. Sodium benzoate is a common preservative and is compatible with Natrosol 250 HHR. For a 30 g transmission gel, a base gel containing 96.10% deionized water, 2.62% hydroxyethylcellulose, 1.16% glycerin, and 0.12% sodium benzoate was made.

Next, 4.05 g of anhydrous calcium chloride was added, raising the temperature to from 23.4° C. to 41.6° C. It took approximately 45 seconds to activate, and the final viscosity after activation at 37° C. was 40800 cP.

A second iteration of this two-part formulation utilized anhydrous magnesium chloride instead of anhydrous calcium chloride. The base gel for this formulation kept the ratio of the hydroxyethylcellulose to water in the base gel the same while keeping the percent of glycerin and sodium benzoate the same in the overall formula. For a 30 g transmission gel, a base gel containing 96.21% deionized water, 2.62% hydroxyethylcellulose, 1.16% glycerin, and 0.12% sodium benzoate was made according to the section below. Next, 1.8 g of anhydrous magnesium chloride was added, raising the temperature to from 22.9° C. to 41.6° C. It took approximately 15 seconds to activate, and the final viscosity after activation at 37° C. was 42800 cP. Because anhydrous magnesium chloride has a much higher standard enthalpy of solution, much less material was needed to achieve the same temperature increase as when anhydrous calcium chloride was substituted. Both the anhydrous calcium chloride and the anhydrous magnesium chloride required about 1.4-1.6 times the theoretical amount of salt (based off thermodynamic data found using Equation 1 and data in Table I), most likely due to heat loss through the package during the activation period, but also possibly due to unavoidable water uptake from exposure to atmosphere during testing. Handling the salts under inert gas during the manufacturing/packaging process might reduce the amount of salt required.

Another option is the formation of a gel by mixing a powder with a second component that is in liquid phase. This requires the use of a thickener that has a lower required temperature for activation KELTROL CG-T is a xanthan gum specifically designed to produce a more transparent gel than most other xanthan gums. Both KELTROL CG-T and the anhydrous salts tested were in the form of a fine powder, so these were mixed to form a homogeneous powder. The water, glycerin, and sodium benzoate were mixed together and then added to the powdered components and then mixed continuously. The temperature immediately rose to 44.1° C. (this slightly higher temperature was chosen in order to help decrease hydration time of the thickener as well as compensate for heat loss through the packaging during the longer activation time). This option would decrease manufacturing costs considerably, but at the cost of a longer activation time (1.5-2 min). Additionally, the gel is not as transparent and is therefore visually distinct as compared to current gel products on the market.

A three phase system for gel warming is described. This option used the same ingredient percentages as Formulations 1 and 2, but separates it into 3 phases in order to decrease the activation time. An amount of water (roughly 40% for each formulation) equal to that from Phase A would be kept as a separate phase (Phase C). Activation of this formula consists of mixing Part B and Part C together, and then be adding this mixture to Part A, and then mixing thoroughly. This decreased the activation time significantly because the dissolution of the salt into water was much faster than dissolution of the salt into a gel. However, the drawback was the final gel formed was not homogenous due to Phase A being too thick. Natrosol 250 HHR has a maximum usage of 3.0%, but when the water is not included in Phase A, Natrosol 250 HHR content increases to about 4.5%. At this concentration the hydroxyethylcellulose is not fully hydrated and the resulting gel is too thick and very clumpy. In order for the further addition of water to be effective, the Natrosol 250 HHR would still need to be fully hydrated, which requires time and a temperature of at least 55° C., thus when Phase CB were mixed in with this thicker form of Phase A, they remained separate and a homogeneous gel was not obtained.

Once the now-mixed gel has reached the desired temperature, the operator opens the casing 22, such as by cutting or tearing off the end of the packet 18A along a line 30 that denotes an end of the two compartments 18, 20A, as depicted here. The heated gel is applied directly to the patient's body, and then the used package 18A is discarded.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A method for applying heated gelatinous material to the skin of a patient, comprising the steps of:
    obtaining a container containing gelatinous material and a heating component, wherein said container comprises:
        a pair of plyable walls bonded to one another around their periphery to form a packet, said packet defined by a top bonded seam and a bottom bonded seam;
        a cut/tear line along said top bonded seam in relative spaced relation thereto;
        a gel compartment formed within said packet and defined by a portion of said top seam at an upper end and a portion of said bottom seam at a lower end, wherein said portion of said top seam forming said upper end of said gel compartment defines a length that is longer than the length defined by said portion of said bottom seam forming said lower end;
        a heating component compartment formed within said packet and defined by a portion of said top seam at an upper end and a lower end bonded seam, wherein said portion of said top seam forming said upper end of said heating component compartment defines a length that is shorter than the length defined by said lower end bonded seam; and
        a frangible seal separating said gel compartment from said heating component compartment;
    activating said heating component by squeezing said packet to breach said frangible seal and mixing said gelatinous material and said heating component whereby said mixed material and heating component produces heat;
    waiting for a sufficient amount of time until said mixed gelatinous material and heating component is heated;
    opening said container and applying said heated gelatinous material to the skin of the patient.

2. The method of claim 1, wherein said heating component of said container obtaining step comprises a module that generates heat as a result of a chemical reaction between two or more chemicals contained within said heating device.

3. The method of claim 1, wherein said heating component of said container obtaining step comprises a material that generates heat responsive to the application of microwaves thereto prior to said activating said heating component step.

4. The method of claim 1, wherein said heating component of said container obtaining step comprises a material that generates heat responsive to the application of Radio Frequency energy thereto prior to said activating said heating component step.

5. The method of claim 1, wherein said heating component of said container obtaining step comprises a material that generates heat responsive to application of a magnetic field thereto prior to said activating said heating component step.

6. The method of claim 1, wherein said heating component of said container obtaining step generates heat in response to physical manipulation.

7. The method of claim 6, wherein said heating component of said container obtaining step comprises a piezoelectric transducer that vibrates responsive to the application of electrical current.

8. A self-heating packet containing gelatinous material, comprising:
    an outer casing comprising a pair of pliable sheets bonded to one another in a generally rectangular shape and having a top seam and an opposing bottom seam interconnecting to a first side seam and a second side seam, and an elongate frangible seal portion extending downwardly from said top seam until it terminates at said first side seam;
    a compartment within said casing containing gelatinous material formed between said top seam, said bottom seam and said second side seam; and
    a heating module contained within said casing in spaced relation to said gelatinous material compartment and separated therefrom by said frangible seal.

9. The self-heating packet of claim 8, wherein said heating module comprises a module that generates heat as a result of a chemical reaction between two or more chemicals contained within said heating module.

10. The self-heating packet of claim 8, wherein said heating module comprises a material that generates heat responsive to the application of microwaves thereto.

11. The self-heating packet of claim 8, wherein said heating module comprises a material that generates heat responsive to the application of Radio Frequency energy thereto.

12. The self-heating packet of claim 8, wherein said heating module comprises a material that generates heat responsive to application of a magnetic field thereto.

13. The self-heating packet of claim 12, wherein said application of a magnetic field thereto generates electrical current that results in said heating module generating heat.

14. The self-heating packet of claim 8, wherein said heating module generates heat in response to physical manipulation.

15. The self-heating packet of claim 14, wherein said module comprises an element that generates physical movement responsive to the application of electrical current thereto.

16. The self-heating packet of claim 15, wherein said physical movement generation element comprises a piezoelectric transducer.

17. An ultrasonic gel packet, comprising:
    an outer casing comprising a pair of pliable sheets bonded to one another in a generally rectangular shape and having a top seam and an opposing bottom seam interconnecting to a first side seam and a second side seam, and an elongate frangible seal portion extending downwardly from said top seam until it term inates at said first side seam;
    non-solid material contained within a first compartment formed between said top seam, said bottom seam and said second side seam, wherein said non-solid material and said heating component material cooperate to generate heat and a gelatinous material when mixed together;
a heating component material contained within a second compartment formed between said top seam and said first side seam; and
a frangible seal portion separating said first compartment from said second compartment.

18. The packet of claim 17, wherein first compartment comprises an upper seam and a lower seam wherein said upper seam is longer in length than the length of said lower seam.

19. The packet of claim 18, wherein said packet is further defined by a cut/tear line traversing said first and second compartments and said frangible seal portion closer in spaced relation to said top seam than it is to said bottom seam.

20. The packet of claim 17, wherein said frangible seal portion defines a length that is greater than said top, bottom and side seams.

\* \* \* \* \*